US00PP32151P2

(12) United States Plant Patent
Hansen

(10) Patent No.: US PP32,151 P2
(45) Date of Patent: Sep. 1, 2020

(54) **X *MANGAVE* PLANT NAMED 'AZTEC KING'**

(50) Latin Name: **x *Mangave***
Varietal Denomination: Aztec King

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,322

(22) Filed: Sep. 13, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373

CPC ... A01H 5/12; A01H 5/02; A01H 5/00; A01H 6/12; A01H 1/02
See application file for complete search history.

(56) References Cited

PUBLICATIONS

Chanticleer Teacup Garden 2019, retrieved on Apr. 2, 2020, retrieved from the Internet at http://chanticleergarden.org/pdffiles/TeacupGarden.pdf, introduction page, p. 3. (Year: 2019).*

* cited by examiner

*Primary Examiner* — June Hwu

(57) ABSTRACT

A new and unique x *Mangave* plant named 'Aztec King' characterized by a large mound of large, broad, fleshy, longitudinally-folded, glaucous-green foliage that is outwardly and cascading toward tips with age, with fine marginal teeth and with large greyed-purple spots that intensify from with greater ultraviolet light exposure. The new plant is suitable for the garden or as a potted plant in the garden or home.

2 Drawing Sheets

Botanical classification: Hybrid; *Manfreda* times *Agave*, known as x *Mangave*.

Variety denomination: 'Aztec King'.

STATEMENT REGARDING PRIOR DISCLOSURES UNDER 37 CFR 1.77(b)(6)

The first non-enabling disclosure of the claimed plant, was on Feb. 14, 2019 in the form of a brief description and picture on a website managed by Walters Gardens, Inc. Walters Gardens, Inc. obtained the new plant and all information about the new plant from the inventor. No plants of x *Mangave* 'Aztec King' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Aztec King' hybridized by the inventor at a wholesale perennial nursery in Zeeland, Mich., USA as cross between a proprietary unreleased hybrid known only by the breeder code x *Mangave* PDN#9 (not patented) as the female or seed parent times an unnamed selection of *Agave ovatifolia* (not patented) as the male or pollen parent. The cross was performed in the Sep. 11, 2012 and seeds were harvested and sown later in December of 2012. Through trials at the same nursery the plant was assigned the breeder code 12-76-5. The new plant has been successfully asexually propagated initially by removal of basal offsets since 2015 at the same nursery in Zeeland, Mich. and also by sterile shoot-tip tissue culture. Both methods of asexual propagation systems have been found to produce stable and identical plants that maintain all the unique characteristics of the original plant.

BRIEF SUMMARY OF THE INVENTION

'Aztec King' differs from its parents as well as all other *Manfreda, Agave* and x *Mangave* known to the applicant. The female parent has foliage that is narrower and more linear, thinner in cross section, has smaller marginal teeth, with more coverage of reddish-purple spots, and the leaves are more arching. The male parent has foliage that is flatter and more compact in habit, with foliage that is more ovate, flatter, with larger marginal teeth, more fibrous, and no mahogany spotting. The nearest comparison plants are: x *Mangave* 'Inca Warrior' (not patented), 'Mission to Mars' U.S. Plant Pat. No. 29,393, 'Falling Waters' U.S. Plant Pat. No. 30,650, and 'Macho Mocha' (not patented). 'Inca Warrior' has less glaucous leaves with larger marginal teeth, and more coverage of greyed-purple spotting. 'Mission to Mars' has a flatter habit, larger foliage that is slightly more cupped, with larger marginal teeth that are tan on young leaves and develop to reddish purple on older leaves, and the spotting becomes denser and more reddish purple with less grey. 'Falling Waters' is a smaller plant with leaves that are more arching and with less greyed-purple spotting. 'Macho Mocha' has longer, narrower foliage with heavier concentration of reddish to reddish-purple spots and a more horizontal habit. Other similar cultivars include: 'Spotty Dotty' U.S. Plant Pat. No. 29,917 is a smaller plant which has foliage that is shorter, narrower and thinner, has a more undulated margin, and the burgundy spotting is more concentrated.

The new plant, 'Aztec King', is unique from all of the above cultivars and all *Agave*, x *Mangave* and *Manfreda* known to the inventor by the following combined traits:

1. Large mound of large, lanceolate, broad, fleshy, longitudinally-folded foliage;
2. Glaucous green foliage has large greyed-purple spots that become more pronounced and overlapping in strong ultraviolet light;
3. Leaf margins finely toothed initially flexible becoming firm with maturity;
4. Moderate growth rate.
5. Foliage outwardly or arching with age.

BRIEF DESCRIPTION OF THE DRAWING

The photograph of x *Mangave* 'Aztec King' demonstrates the overall appearance of the new plant including the unique traits of the new plant with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
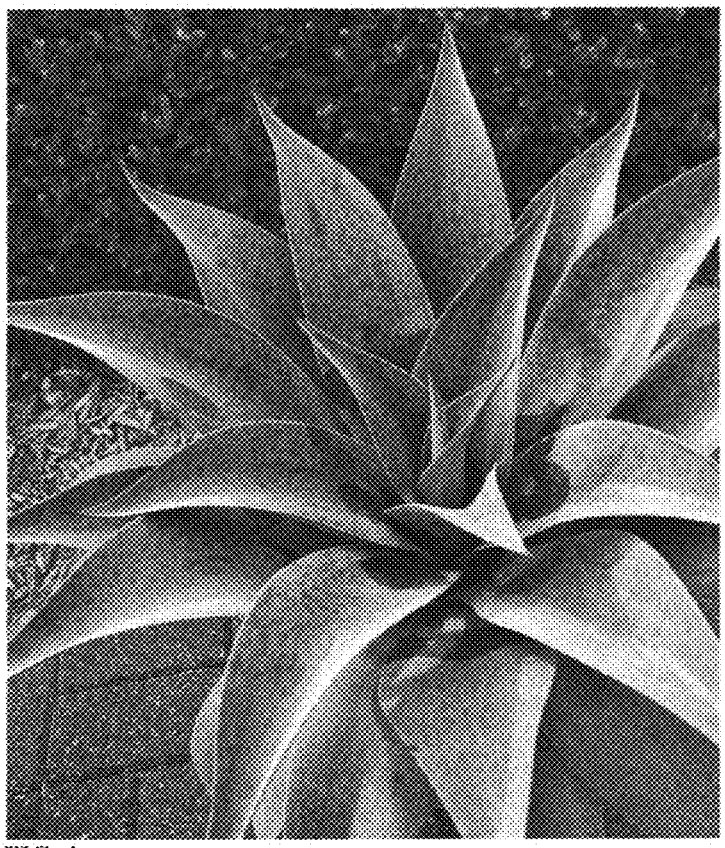
FIG. 1 shows the new plant as a four-year-old grown in a greenhouse.
Figure 2:
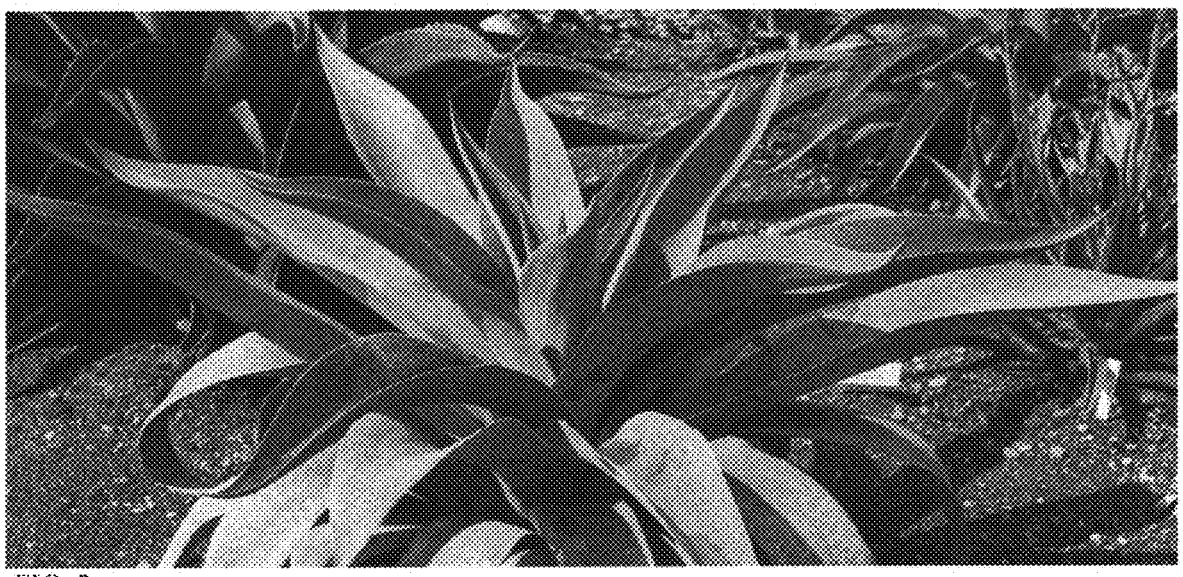
FIG. 2 shows the new plant as a six-year-old grown in a greenhouse followed by a season in a full sun trial garden.
Figure 3:
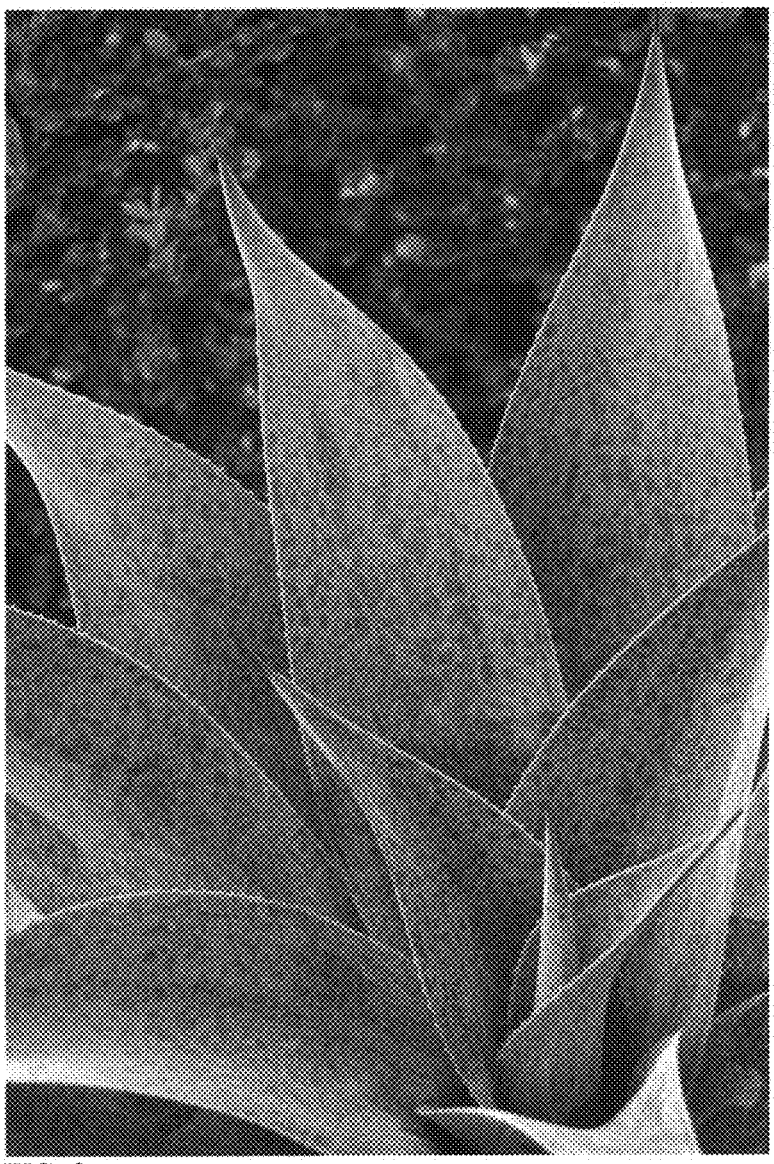
FIG. 3 shows a close-up of the foliage of a four-year-old grown in a greenhouse.

The following descriptions and color references are based on the 2015 edition of The Royal Horticultural Society Colour Chart except where common dictionary terms are used. The new plant, x *Mangave* 'Aztec King', has not been observed under all possible environments. The phenotype may vary slightly with different environmental conditions, such as temperature, light, fertility, moisture and maturity levels, but without any change in the genotype. The following observations and size descriptions are of a six-year old plant in a full-sun trial garden having been grown during the fall through spring in a commercial wholesale greenhouse in Zeeland, Mich. with supplemental water and fertilizer as needed.

Parentage: An cross between a proprietary unreleased hybrid known only by the breeder code x *Mangave* PDN#9 as the female or seed parent times an unnamed selection of *Agave ovatifolia* (not patented) as the male or pollen parent;

Propagation: By sterile shoot-tip tissue culture;

Time to initiate roots from tissue culture: About 21 to 28 days;

Growth rate: Moderate;

Crop time: About 20 to 24 weeks to finish in a 3.8 liter container from a 35 mm tissue culture growing at about 21° C.;

Rooting habit: Fleshy, lightly branching, with roots up to 40 cm long;

Root color: Nearest RHS 158C;

Plant shape and habit: Succulent herbaceous perennial with basal rosettes of about 48 leaves radially emerging outwardly from central stem and arching distally, producing a radially-symmetrical, rounded mound;

Plant size: Foliage height about 70.0 cm tall from soil line to the top of the leaves and about 116.0 cm wide at the widest point slightly below soil line in container;

Foliage description: Lanceolate; simple; sessile; sarcous; bi-laterally symmetrical; apex acute with terminal spine; terminal spine to about 12.0 mm long; base truncate; longitudinally conduplicate, especially young leaves; margins finely dentate with teeth slightly curved toward stem; glaucous waxy bloom abaxial and adaxial without trichomes; with adaxial spots about 10.0 mm long to 5.0 mm wide frequently touching or overlapping and abaxial spots to 5.0 mm long and 4.0 mm wide;

Teeth: Initially flexible, becoming hard and sharp with age; about 1.5 mm long and about 2.0 mm wide at base; average about 6.0 mm apart in middle of mature leaves and about 2.0 mm apart near base;

Leaf size: To about 69.0 cm long, about 14.0 cm wide toward middle, about 5.0 cm deep and 2.0 cm thick near base; average about 64.0 cm long, 12.0 cm wide and 2.0 mm thick;

Foliage fragrance: None observed;

Leaf number: About 48 per plant;

Leaf blade color:

*Adaxial* (*young*).—Nearest RHS 137C with spots nearest RHS N187B to RHS 187B in low ultraviolet light intensifying with high ultraviolet exposure to nearest RHS N187A.

*Abaxial* (*young*).—Nearest RHS 137C with spots nearest RHS N187B to RHS 187B in low ultraviolet light intensifying with high ultraviolet exposure to nearest RHS N187A.

*Adaxial* (*mature*).—Between RHS 146D and RHS 147C with spots intensifying with ultraviolet light exposure nearest RHS N187A.

*Abaxial* (*mature*).—Nearest RHS 138A and spots to nearest RHS N187A.

*Teeth*.—Beginning nearest RHS 161D and maturing to between RHS 166A and RHS 166B.

*Terminal spine color*.—On young emerging leaves between RHS N163A and RHS 169A, on mature leaves nearest RHS 200A.

Petiole: Leaves sessile;

Veins: Parallel; not distinct abaxial or adaxial;

Flower description: Not yet observed to date;

Fruit and seed not observed to date;

Disease resistance: x *Mangave* 'Aztec King' has not been observed to be resistant to diseases beyond that which is normal for x *Mangave, Agave* or *Manfreda*. The new plant is xeromorphic and survives well with minimal water once established. The new plant is estimated to be cold hardy at least from USDA zone 9. Full extent of winter hardiness has not been tested.

It is claimed:

1. A new and distinct cultivar of ornamental x *Mangave* plant named 'Aztec King' as herein described and illustrated.

* * * * *